United States Patent
Hänni et al.

(10) Patent No.: US 6,730,199 B1
(45) Date of Patent: May 4, 2004

(54) APPARATUS FOR MEASURING THE ELECTROPHYSIOLOGICAL ACTIVITY OF A GROUP OF CELLS

(76) Inventors: Claude Hänni, 80, rue de la Charrière, CH-2300 La Chaux-De-Fonds (CH); Luc Stoppini, 26, rue Carteret, CH-1202 Geneva (CH)

( * ) Notice: Subject to any disclaimer, the term of this patent is extended or adjusted under 35 U.S.C. 154(b) by 0 days.

(21) Appl. No.: 09/701,904

(22) PCT Filed: Jun. 4, 1999

(86) PCT No.: PCT/CH99/00244
§ 371 (c)(1),
(2), (4) Date: Dec. 5, 2000

(87) PCT Pub. No.: WO99/64858
PCT Pub. Date: Dec. 16, 1999

(30) Foreign Application Priority Data

Jun. 8, 1998 (FR) .............................. 98 07595

(51) Int. Cl.[7] .............................................. G01N 27/327
(52) U.S. Cl. ........................ 204/403.02; 204/403.01; 204/403.13; 204/406; 204/408; 435/287.1; 435/288.7
(58) Field of Search ................... 204/403.01, 403.02, 204/403.13, 406, 408, 407; 435/287.1, 288.7

(56) References Cited

U.S. PATENT DOCUMENTS

| 4,225,410 | A |   | 9/1980  | Pace |
| 5,563,067 | A | * | 10/1996 | Sugihara et al. ......... 435/287.1 |
| 5,810,725 | A | * | 9/1998  | Sugihara et al. ............ 600/372 |
| 5,981,268 | A | * | 11/1999 | Kovacs et al. ............ 435/287.1 |
| 6,113,768 | A | * | 9/2000  | Fuhr et al. .................. 204/643 |

FOREIGN PATENT DOCUMENTS

| WO | 85 02257 | 5/1985 |
| WO | 96 10740 | 4/1996 |

* cited by examiner

Primary Examiner—Kaj K. Olsen
(74) Attorney, Agent, or Firm—Davis & Bujold, PLLC

(57) ABSTRACT

The invention concerns an apparatus (10) comprising essentially a support (11) wherein is placed a measuring card (12), a perfusion device (13), a thermostat (14), a measuring box (15) and a measurement management system (16). The measuring card (12) comprises an electrode array whereof one end emerges into the chamber and the other end is placed outside said chamber. The group of cells is placed in the chamber which is connected to the perfusion device (13). The support (11) comprises a connector (25) connecting the card (12) electrodes to the measurement management system (16) via the measuring box (15).

13 Claims, 2 Drawing Sheets

APPARATUS FOR MEASURING THE ELECTROPHYSIOLOGICAL ACTIVITY OF A GROUP OF CELLS

The present invention concerns an apparatus for measuring the electrophysiological activity of a mass of cells.

BACKGROUND OF THE INVENTION

In order to measure the electrophysiological activity of a mass of cells, the cells are placed in a measurement device consisting of an electrode network. Each electrode in the network comprises a bare zone contacting the cell mass, a bare zone accessible from the outside of a container holding the cells, and an insulated zone separating the two bare zones.

Various devices have been developed, generally in the form of laboratory devices, to perform measurements of said electrophysiological activity.

These devices have several disadvantages. In particular, the structure of the container does not allow long term cells survival. Additionally, when a user wishes to measure electrophysiological cell activity, he places electrical supply points in contact with the involved electrodes in the electrode network. This contact is established manually. That means it is particularly difficult to take measurements over a specific time period or simultaneously on several electrodes.

When one area on the group of cells must be stimulated, the stimulation is performed manually using a stimulation electrode. This complicates the measurement and precludes taking remote measurements. Finally, this device does not provide an on line analysis of the measurement results.

SUMMARY OF THE INVENTION

The present invention proposes eliminating these disadvantages with an apparatus that is simple to manipulate, versatile, and completely capable of remote control. This apparatus also allows long term cell survival so that measurements can be taken over a long time period.

This goal is achieved with an apparatus such as the one described in the preamble, characterized in that it comprises a measurement card with a chamber which receives the cells for analysis and contains a network of electrodes, at least some of which contact said cell mass, comprising a connector formed of conductive tracks, with each electrode in the electrode network being connected to a conductive track on the connector and said connector being coupled with a measurement circuit which transmits electrical signals to at least one electrode on said electrode network and receives electrical signals from at least one of the electrodes.

According to a preferred embodiment, the electronic measurement circuit is connected to a measurement management system which controls measurement parameters and analyzes measurement signals.

The apparatus advantageously comprises a means for assigning at least one electrode in the electrode network an electrode measurement function, and a means for assigning at least one electrode in the electrode network an electrode stimulation function.

The card is preferably placed in a support and the connector is integral with said support. The support is advantageously made of metal.

According to an advantageous embodiment, the support cooperates with a heating means which heats the measurement card.

The measurement card advantageously cooperates with a perfusion device which perfuses said cell mass.

According to a preferred embodiment, the management system comprises a means for controlling the perfusion device and a heating means. It also comprises a remote control.

The apparatus advantageously comprises a viewing means which preferably consists of a camera.

BRIEF DESCRIPTION OF THE DRAWINGS

The present invention and its features will be better understood with reference to a specific embodiment of the invention and to the attached drawings, in which.

DESCRIPTION OF THE PREFERRED EMBODIMENTS

Figure 1:
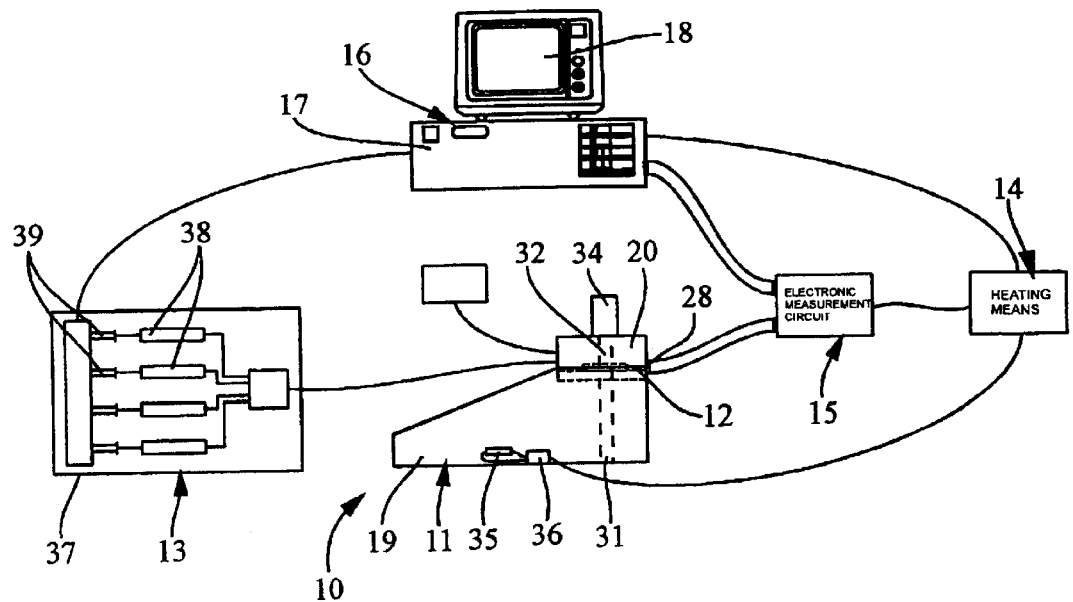
FIG. 1 is a view of the entire apparatus of the invention.
Figure 2:
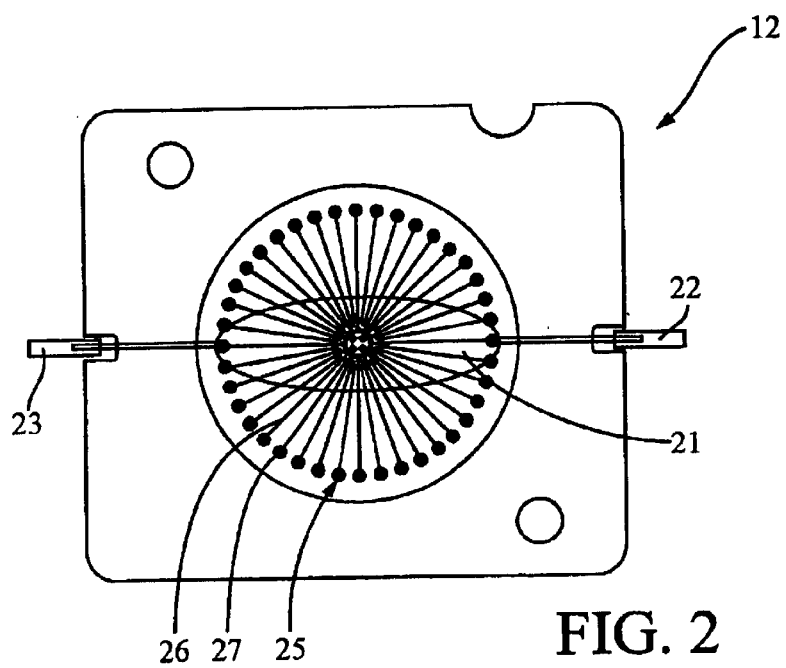
FIG. 2 is a view of a measurement card used with the apparatus of FIG. 1.
Figure 3:
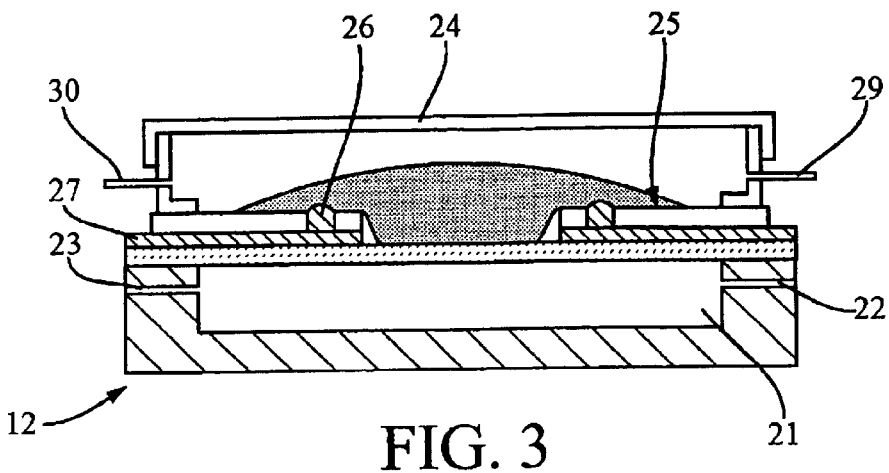
FIG. 3 is a cross-section of the measurement card of FIG. 2.

With reference to these drawings, the apparatus 10 essentially consists of a support 11 in which a measurement card 12 is placed, along with a perfusion device 13, a heating means 14, an electronic measurement circuit 15, and a measurement management system 16 which may consist of a computer 17 and a monitor 18.

Support 11 essentially consists of a fixed portion 19, in which measurement card 12 is placed, and a movable portion 20. The measurement card essentially consists of a chamber 21 with an inlet 22 and an outlet 23, containing the cells for analysis, a removable cover 24 which seals the chamber, and an electrode network 25. The electrodes forming this network have a first portion 26 located inside the chamber so it can contact with certain cells in the cell mass, and a second portion 27 located outside the chamber. The movable portion 20 of the support is integral with a flexible electronic circuit formed of a network of conductive tracks, one extremity of which contacts a respective electrode on the measurement card. The other extremity of the tracks of the network of conductive tracks is placed in a connector 28 attached to the support. This support is advantageously made of metal and forms a Faraday cage around the card. The chamber may also comprise a gas injection duct 29 and a gas exhaust duct 30. This is for introducing gas into the chamber.

The support has a hole 31 through its fixed portion and a hole 32 through its movable portion. These holes are aligned and arranged so that the chamber in the measurement card is placed between the two holes when the support is closed.

The support may be associated with a lighting and/or a viewing device 33. Said viewing device may consist of a camera 34, particularly a digital camera, making it possible to either observe the analyzed cells with a microscope or a magnifier, or to project an image on monitor 18 of computer 17.

The support also contains a heater 14 as well as a temperature control means 35. The heater 14 may be in the form of an electrical resistor positioned so as to heat a support zone near the cells to be analyzed. It may also consist of channels formed in the support itself for circulating hot air generated by a ventilator associated with a heating resistor. The temperature controls means 35 is connected to a thermostat 36 and may consist of a thermostatic sensor located near the cells to be analyzed.

When a cell sample is put in place for measurement, it is located in chamber 21 of the card. Removable cover 24 is closed, movable support portion 20 is removed to allow card 12 to be placed in the support, then movable support portion 20 is replaced, closing the support.

The chamber inlet 22 and outlet 23 are respectively connected to a flexible inlet tube and a flexible exhaust tube. The inlet tube is connected to perfusion device 13. Said perfusion device is used first, to deliver liquid nutrient to the cells located in the card and second, to administer a product for testing to the cells.

Said perfusion device is formed of a support 37 containing one or more syringes 38 and actuators 39 which independently activate the syringe pistons. Piston movement is controlled by measurement management system 16 so that the desired product is delivered at any given instant or over any given time period, in a certain quantity or at a certain rate.

Depending upon the measurements to be performed or the nature of the cells or of the products to be tested, a gas may be introduced through gas injection duct 29. It is also possible to generate gas flow into the chamber by introducing gas through duct 29 and exhausting it through gas exhaust duct 30.

Thermostat 36 defines a given temperature or temperature evolution over time. It is also controlled by measurement management system 16 and acts on the heater.

The electronic measurement circuit 15 is an interface between measurement management system 16 and measurement card 12. This circuit amplifies and multiplexes the electrical signals being displaced in both directions between the card and the measurement management system.

Said electronic measurement circuit comprises a means for amplifying the electrical signals circulating between the card and the management system. It also comprises a means for modifying the amplification factor, as well as the multiplex order. These modifications can be made using measurement management system 16, that is, without any mechanical action on the electronic measurement circuit. It should be noted that the circuit may also be made in the form of an electronic card integrated into measurement management system 16.

The measurement control system 16 comprises processor 17, which uses measurement software specifically designed for the application desired. Specifically, the software controls the operation of perfusion device 13, heater 14, and electronic measurement circuit 15. It also assigns different functions to the electrodes. More specifically, in a concrete embodiment, two electrodes are chosen as stimulation electrodes. An electrical signal is thus sent from the electronic measurement circuit to these electrodes. Other electrodes, for example, eight of the forty total electrodes forming the circuit, are used as measurement electrodes. An electrical signal originating from the card is thus received by the electronic circuit. The choice of electrodes depends upon the organization of the tissue.

It is also possible to reserve one or more electrodes as bio-sensors in order to detect the presence and/or concentration of a given product.

In order to be able to see the organization of the tissues and make a judicious choice of electrodes, it is important to provide a viewing means, either a direct view through a transparent portion or a camera 34 which can project of an image on screen 18.

The management system provides simple definition of all parameters relative to the measurements performed. During electrical stimulation, the length, period, and amplitude of the impulses can be specifically defined. Stimulation can also be accomplished using an external device to program the different parameters.

The data for effecting measurements, as well as the results of these measurements, can be stored in a storage unit placed in measurement management system 16. This allows the data to be stored and analyzed later.

Figure 4:
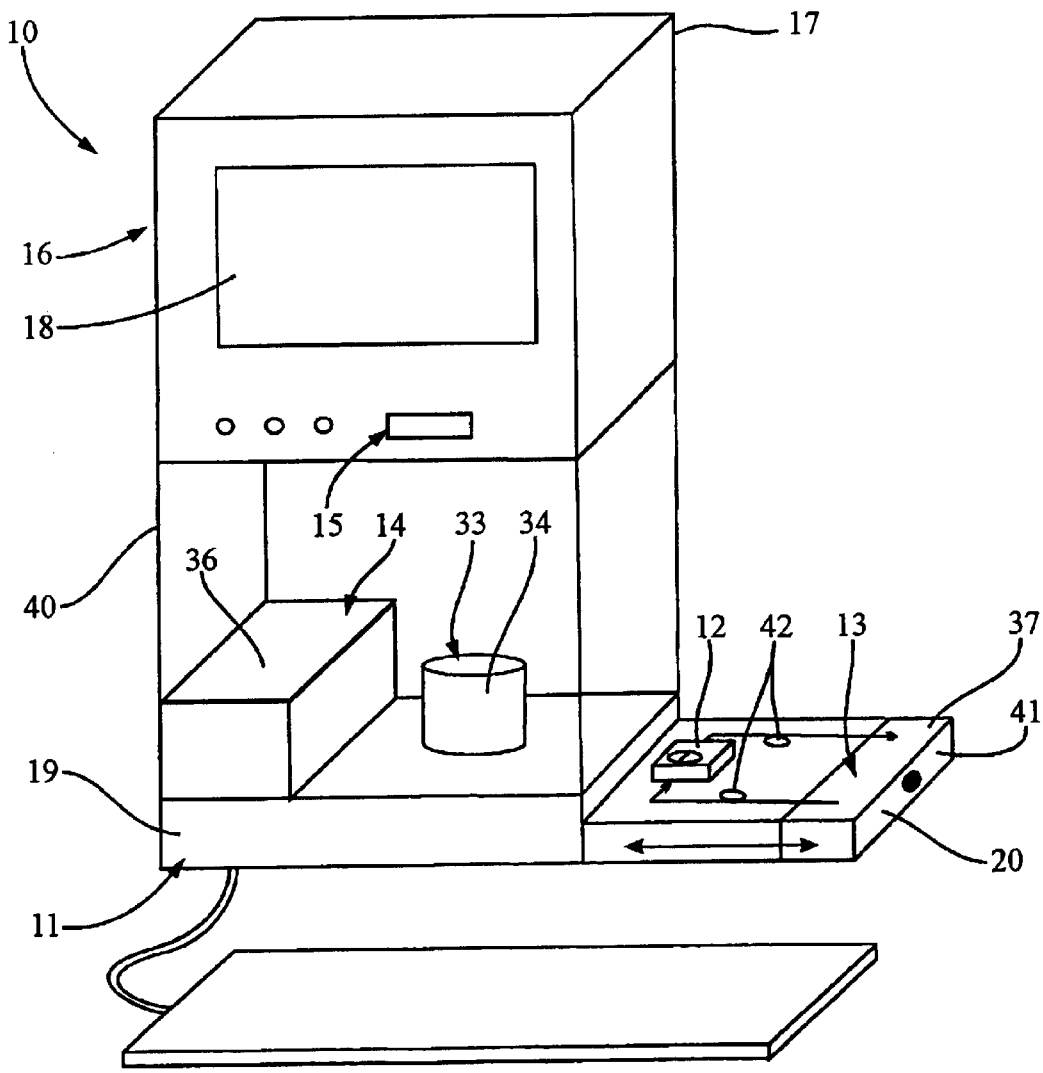
FIG. 4 is a schematic view of a specific embodiment of the invention.

The embodiment shown in FIG. 4 represents the "monoblock" version of apparatus 10 of the invention.

This apparatus comprises a chassis 40 within which are located support 11 receiving measurement card 12, perfusion device 13, heater 14, thermostat 36, electronic measurement circuit 15, measurement management device 16, and viewing means 33.

Support 11 has a drawer 41 which opens for placement of measurement card 12 and access to perfusion device 13. When drawer 41 is closed, measurement card 12 is located opposite camera 34.

In the embodiment shown, perfusion device 13 comprises peristaltic pumps 42.

The monoblock embodiment is advantageous primarily because it is very compact.

The present invention offers a certain number of advantages over existing systems. In particular, the apparatus is very simple to manipulate. Placing the cart in the support actually assures the electrical connection of all the electrodes in the network. The choice of electrodes used is made simply using management system 16. The images from the viewing camera are displayed on screen 18. For this reason it is possible, by using the appropriate computer program, to individually assign a function to each electrode using a pointer on the screen.

In the same way, it is possible to program functions for each electrode. These functions might vary over a period of time according to a predefined program.

In addition, it is possible to control all the operations of the apparatus, such as temperature, temperature variations, activating each of the syringe plungers or peristaltic pumps, with computer 17.

All the parameters are introduced through this management system, which also can be remote-controlled using a modem.

Additionally, thanks to the viewing device, the choice of electrodes as a function of tissue organization, as well as surveillance of cell survival, can all be done from a distance.

Since the measurement card is closed by a cover and placed in a support, the cells are insulated from the exterior environment and therefore the measurements can be performed in a non-sterile environment.

The support is advantageously made of metal. Thus, it serves as a Faraday cage, eliminating the necessity of adding another Faraday cage.

The present invention is not limited to the embodiment described, but extends to any modification or variation obvious to a person skilled in the art.

In particular, other functions such analysis of certain particular measurement parameters, may be integrated into the software in management system 16.

The entire apparatus can also be adapted to specific cases where measurements are taken—for example, if viewing from a particular perspective is not necessary, or if the apparatus is always used for the same type of measurement requiring specific conditions.

It is also possible to place the measurement card in a microscope support. An electrical cord extends to connect the measurement card with support 11, allowing the card to be used outside its support.

The number and disposition of the electrodes can also be modified according to analysis requirements.

What is claimed is:

1. An apparatus for measuring electrophysiological activity in a mass of cells, the apparatus comprising:

a measurement card (12) with a chamber (21) for receiving the cells for analysis, and the measurement card contains a network of electrodes (25), at least some of the electrodes (25) being located for contact with the mass of cells during operation of the apparatus, each electrode (25) comprising a connector (28) formed of a plurality of conductive tracks, and each electrode (25) of the electrode network being in contact with one the plurality of conductive tracks on the connector;

the connector (28) being coupled with an electronic measurement circuit (15) which transmits electrical signals to at least one the plurality of electrodes in the electrode network, and the electronic measurement circuit (15) receiving electrical signals from at least one of the plurality of electrodes; and the chamber (21) has a cover for closing the chamber (21), a wall of the chamber (21) having an inlet (22) for supplying, from a perfusion device, one of a nutrient and a product for testing the cells to the chamber (21), and a wall of the chamber (21) having an outlet (23) for removing by products from the chamber (21), the chamber (21) further including an gas injection duct (29) for supplying a gas to the chamber (21) and a gas exhaust duct (30) for removing gas from the chamber (21).

2. The apparatus according to claim 1, wherein the electronic measurement circuit (15) is connected to a measurement management system (16) which analyzes the electrical signals and controls measurement parameters.

3. The apparatus according to claim 2, wherein the measurement management system (16) comprises means for controlling the perfusion device (13)) which perfuses the mass of cells during operation of the apparatus.

4. The apparatus according to claim 3, wherein the management system (16) comprises remote control means for regulation of the management system (16).

5. The apparatus according to claim 2, wherein the measurement management system (16) comprises heating means (14) for heating the cells in the measurement card (12) during operation of the apparatus.

6. The apparatus according to claim 1, wherein the apparatus comprises means for assigning an electrode measurement function to at least one the plurality of electrodes in the electrode network (25).

7. The apparatus according to claim 1, wherein the apparatus comprises means for assigning an electrode stimulation function to at least one the plurality of electrodes in the electrode network (25).

8. The apparatus according to claim 1, wherein the measurement card (12) is carried by a support (11) and the connector (28) is integral with the support (11).

9. The apparatus according to claim 8, wherein the support (11) is made of metal.

10. The apparatus according to claim 8, wherein the support (11) has heating means (14) which heats the mass of cells in the measurement card (12) during operation of the apparatus.

11. The apparatus according to claim 1, wherein the measurement card (12) cooperates with the perfusion device (13) which perfuses the mass of cells during operation of the apparatus.

12. The apparatus according to claim 1, wherein the apparatus further comprises viewing means (33) for viewing analyzed cells.

13. The apparatus according to claim 12, wherein the viewing means (22) comprises a camera (34).

\* \* \* \* \*